United States Patent [19]

Wallach

[11] Patent Number: 5,104,736
[45] Date of Patent: * Apr. 14, 1992

[54] REINFORCED PAUCILAMELLAR LIPID VESICLES

[75] Inventor: Donald F. H. Wallach, Brookline, Mass.

[73] Assignee: Micro-Pak, Inc., Wilmington, Del.

[*] Notice: The portion of the term of this patent subsequent to Mar. 27, 2090 has been disclaimed.

[21] Appl. No.: 371,738

[22] Filed: Jun. 26, 1989

Related U.S. Application Data

[63] Continuation-in-part of Ser. No. 157,571, Mar. 3, 1988, Pat. No. 4,911,928, which is a continuation-in-part of Ser. No. 25,525, Mar. 13, 1987, abandoned, and a continuation-in-part of Ser. No. 78,658, Jul. 28, 1987, Pat. No. 4,855,090, and a continuation-in-part of Ser. No. 124,824, Nov. 25, 1987, Pat. No. 4,917,951.

[51] Int. Cl.$^5$ ............... A61K 9/127; B01J 13/02; B01J 13/16
[52] U.S. Cl. ............... 428/402.2; 264/4.3; 264/4.32; 264/4.33; 264/427; 424/450; 436/829
[58] Field of Search ............... 264/4.3, 4.32, 4.33, 264/4.7; 428/402.2; 424/450; 436/829

[56] References Cited

U.S. PATENT DOCUMENTS

| | | | |
|---|---|---|---|
| 3,069,370 | 12/1962 | Jensen et al. | 264/4.1 X |
| 3,372,201 | 3/1968 | Leary et al. | 568/618 |
| 3,957,971 | 5/1976 | Oleniacz | 424/70 |
| 4,021,364 | 5/1977 | Speiser et al. | 264/4.7 X |
| 4,133,874 | 1/1979 | Miller et al. | 428/402.2 X |
| 4,182,330 | 1/1980 | Michaels | 128/260 |
| 4,217,344 | 8/1980 | Vanlerberghe et al. | 424/450 |
| 4,235,871 | 11/1980 | Papahadjopoulos et al. | 424/450 |
| 4,241,046 | 12/1980 | Papahadjopoulos et al. | 424/450 X |
| 4,247,411 | 1/1981 | Vanlerberghe et al. | 264/4.6 |
| 4,348,329 | 9/1982 | Chapman | 260/463 |
| 4,356,167 | 10/1982 | Kelly | 424/450 |
| 4,377,567 | 3/1983 | Geho | 424/1.1 |
| 4,448,765 | 5/1984 | Ash et al. | 424/450 |
| 4,485,045 | 11/1984 | Regen | 264/4.7 X |
| 4,485,054 | 11/1984 | Mezei et al. | 264/4.6 |
| 4,536,324 | 8/1985 | Fujiwara et al. | 252/311 |

(List continued on next page.)

FOREIGN PATENT DOCUMENTS

| | | |
|---|---|---|
| 0032578 | 7/1984 | European Pat. Off. |
| 0167825 | 1/1987 | European Pat. Off. |
| 3410602 | 9/1984 | Fed. Rep. of Germany |
| 59-106423 | 6/1984 | Japan |
| 61-207324 | 9/1986 | Japan |
| 85/01440 | 4/1985 | PCT Int'l Appl. |
| 87/06499 | 11/1987 | PCT Int'l Appl. |
| 1539625 | 1/1979 | United Kingdom |
| 2147263 | 5/1985 | United Kingdom |
| 2198947 | 6/1988 | United Kingdom |

OTHER PUBLICATIONS

*Diffusion of Univalent Ions Across the Lamellae of Swollen Phospholipids* A. Bingham et al., J. Mol. Biol. 13, 238–252 (1965).

(List continued on next page.)

Primary Examiner—Richard D. Lovering
Attorney, Agent, or Firm—Lahive & Cockfield

[57] ABSTRACT

Disclosed are paucilamellar lipid vesicles reinforced with polyacrylamide, and methods of producing the same. The vesicles include about 2–10 lipid bilayers in the form of substantially spherical shells separated by a plurality of aqueous layers. Each of the bilayers have a layer of polyacrylamide lining its innermost side. The bilayers and the aqueous layers surround a large, substantially amorphous central cavity containing a water-immiscible oily phase or a polyacrylamide core. The method of the invention includes forming a lipophilic phase containing a surfactant and a lipid-soluble material to be encapsulated or to be incorporated into the lipid structure of the vesicle, forming an aqueous phase containing polyacrylamide; shear mixing the lipophilic phase and the aqueous phase, thereby forming a plurality of paucilamellar lipid vesicles containing acrylamide in their aqueous regions; separating the vesicles from any unincorporated vesicle constituents; and polymerizing the acrylamide in the aqueous layers of the vesicles. A method of encapsulating a water-soluble material is also disclosed.

21 Claims, 1 Drawing Sheet

U.S. PATENT DOCUMENTS

| | | | |
|---|---|---|---|
| 4,544,545 | 10/1985 | Ryan et al. | 424/1.1 |
| 4,551,288 | 11/1985 | Kelly | 264/4.6 |
| 4,564,599 | 1/1986 | Janoff et al. | 436/507 |
| 4,605,630 | 8/1986 | Kung et al. | 436/829 X |
| 4,608,211 | 8/1986 | Handjani et al. | 264/4.6 |
| 4,610,868 | 9/1986 | Fountain et al. | 424/1.1 |
| 4,619,913 | 10/1986 | Luck et al. | 514/2 |
| 4,684,625 | 8/1987 | Eppstein et al. | 514/19 |
| 4,692,433 | 9/1987 | Hostetler et al. | 514/12 |
| 4,695,554 | 9/1987 | O'Connell et al. | 436/528 |
| 4,725,442 | 2/1988 | Haynes | 424/490 |
| 4,731,210 | 3/1988 | Weder et al. | 264/4.3 |
| 4,744,989 | 5/1988 | Payne et al. | 424/490 |
| 4,772,471 | 9/1988 | Vanlerberghe et al. | 424/450 |
| 4,830,857 | 5/1989 | Handjani et al. | 424/450 |
| 4,839,111 | 6/1989 | Huang | 264/4.3 X |
| 4,855,090 | 8/1989 | Wallach | 264/4.3 X |
| 4,911,928 | 3/1990 | Wallach | 424/450 |

OTHER PUBLICATIONS

*McCutcheon's Detergents & Emulsifiers 1973 North American Edition*, p. 27.

*The Carrier Potential of Liposomes in Biology and Medicine* (First of Two Parts), G. Gregoriadis, The New England Journal of Medicine, 295, 704–710 (1976).

*Procedure for Preparation of Liposomes with Large Internal Acqueous Space and High Capture by Reverse-Phase Evaporation*, F. Szoka, Jr. et al., Proc. Natl. Acad. Sct. USA 75, 4194–4198 (1978).

*Methodes de Preparation des Liposomes*, N. Douseet et al., Puisieux and Delattre, Eds. Techniques et Documentation La Voisier Paris, pp. 41–72, (1985).

*McCutcheon's Emulsifiers & Detergents 1982 North American Edition*, pp. 76–77.

*Liposomes*, edited by Marc J. Ostro, The Liposome Co., Princeton, NJ, Marcel Dekker, Inc., New York and Basel, pp. 246–249 (1983).

*A Very Mild Method Allowing the Encapsulation of Very High Amounts of Macromolecules into Very large (1000 nm) Unilamellar Liposomes*, Philippot et al., Biochem. Biophys. Acta, 734, 137–143 (1983).

*Bilayer Fluidity of Non-Ionic Vesicles. An Investigation by Differential Polarized Phase Fluorometry*, A. Ribier et al., Colloids and Surfaces 10 155–161 (1984).

*The Preparation and Properties of Niosomes—non-ionic Surfactant Vesicles*, A. Baillie et al., J. Pharm. Pharmacol, 37, 863–888 (1985).

*11 Les Niosomes*, R. Handjani-Vila et al., Les Liposomes, Puisieux and Delattre, Eds. Techniques et Documentation La Voisier Paris, pp. 297–313 (1985).

*Extemporaneous Preparation of Large Unilamellar Liposomes*, J. Philippot et al., Biochem. Biophys. Acta, 821, 79–84 (1985).

*Problemes technologiques poses par l'utilisation des Liposomes Commevecteurs de Substances Medicamenteuses. Encapsulation, sterilisation, conservation.*, F. Puisieux et al., Les Liposomes, Eds. Techniques et Documentation La Voisier Paris, pp. 73–113 (1985).

*Non-Ionic Surfactant Vesicles, Niosomes, as a Delivery System for the Anti-Leishmanial Drug, Sodium Stibogluconate*, A. Baillie et al., J. Pharm. Pharmacol, 38, 502–505, (1986).

REINFORCED PAUCILAMELLAR LIPID VESICLES

REFERENCE TO RELATED APPLICATIONS

This application is a continuation-in-part of U.S. Pat. application Ser. No. 157,571, filed Mar. 3, 1988, entitled "Paucilamellar Lipid Vesicles", which is a continuation-in-part of U.S. Pat. application Ser. No. 025,525, filed Mar. 13, 1987, entitled "Method of Producing High Aqueous Volume Multilamellar Vesicles", now abandoned, U.S. Pat. application Ser. No. 078,658, filed July 28, 1987, also entitled "Method of Producing High Aqueous Volume Multilamellar Vesicles", now U.S. Pat. No. 4,855,090, and U.S. Pat. application Ser. No. 124,824, filed Nov. 25, 1987, entitled "Lipid Vesicles Formed of Surfactants and Steroids", now U.S. Pat. No. 4,917,951.

BACKGROUND OF THE INVENTION

The present invention relates to the production of paucilamellar lipid vesicles. More particularly, the present invention relates to a method of producing reinforced paucilamellar lipid vesicles with added mechanical strength. These reinforced vesicles have an unstructured central cavity surrounded by 2-10 lipid bilayers. Each of the bilayers has a layer of polyacrylamide lining its innermost side. The central cavity may include a water-immiscible oily phase or an aqueous-soluble material and/or polyacrylamide.

Lipid vesicles are substantially spherical structures made of materials having a high amphiphilic lipid content, e.g., surfactants or phospholipids. There are a variety of uses for lipid vesicles including the use as adjuvants or as carriers for a wide variety of materials. The lipids of these spherical vesicles are organized in lipid bilayers which encapsulate an aqueous volume. The aqueous volume is interspersed between multiple onion-like shells of lipid bilayers (forming multilamellar lipid vesicles or "MLV") or is contained within an amorphous central cavity. The most commonly known lipid vesicles having an amorphous central cavity filled with aqueous medium are the unilamellar lipid vesicles. As the name indicates, unilamellar vesicles have a single lipid bilayer. Large unilamellar vesicles ("LUV") generally have a diameter greater than about $1\mu$ while small unilamellar lipid vesicles ("SUV") generally have a diameter of less than $0.2\mu$.

Although substantially all the investigation of lipid vesicles in recent years has centered on multilamellar and the two types of unilamellar lipid vesicles, a fourth type of lipid vesicle, the paucilamellar lipid vesicle ("PLV"), exists. This lipid vesicle has barely been studied heretofore and has only been manufactured previously with phospholipids. PLV's consist of about 2 to 10 peripheral bilayers surrounding a large, unstructured central cavity. In all the previously described PLV's, this central cavity was filled with an aqueous solution (Callo and McGrath, Cryobiology 1985, 22(3), pp. 251-267).

Each type of lipid vesicle appears to have certain uses for which it is better adapted. For example, MLV's have a higher structural lipid content then any of the other lipid vesicles so to the extent that a lipid vesicle can encapsulate or carry a lipophilic material within the bilayers, MLV's have been deemed the most advantageous for carrying lipophilic materials. In contrast, the amount of water encapsulated in the aqueous shells between the lipid bilayers of the MLV's is much smaller than the water which can be encapsulated in the central cavity of LUV's, so LUV's have been considered advantageous in transport of aqueous material. However, LUV's, because of their single lipid bilayer structure, are not as physically durable as MLV's and are more subject to enzymatic degradation. SUV's have neither the lipid or aqueous volumes of the MLV's or LUV's but because of their small size have easiest access to cells in tissues.

PLV's, which can be considered a subclass of the MLV's, are a hybrid having features of both MLV's and LUV's. PLV's appear to have advantages as transport vehicles for many uses as compared with the other types of lipid vesicles. In particular, because of the large, unstructured central cavity, PLV's are easily adaptable for transport of large quantities of encapsulated materials. However, the multiple lipid bilayers of the PLV's provides PLV's with the capacity to transport a greater amount of lipophilic material in their bilayers as well as with additional physical strength and resistance to degradation as compared with the single lipid bilayer of the LUV's. However, conventional PLV's are more fragile than MLV's because of the fewer number of bilayers. The central cavity of the PLV's of the present invention can be filled wholly or in part with an apolar oil or wax and then can be used as a vehicle for the transport or storage of lipophilic materials. The amount of lipophilic material which can be transported by the PLV's with an apolar core is much greater than can be transported by MLV's.

Conventional methods of producing multilamellar lipid vesicle start by dissolving the lipids, together with any lipophilic additives, in an organic solvent. The organic solvent is then removed by evaporation using heat or by passing a stream of an inert gas (e.g., nitrogen) over the dissolved lipids. The residue is then hydrated with about an equivalent of an aqueous phase, generally containing electrolytes and additives such as hydrophilic biologically-active materials, to form a separable hydrated lamellar phase. This lamellar phase is then dispersed into an excess of an aqueous phase to form large multilamellar lipid membrane structures. In some variations, different types of particulate matter or structures have been used during the evaporation process to assist in the formation of the lipid residue. Those in the field have shown that by changing the physical structure of the lipid residue, better vesicles form upon hydration. Two recent review publications (Gregoriadis, G., ed. *Liposome Technology* (CRC, Boca Raton, Fl.), Vols. 1-3 (1984); and Dousset and Douste-Blazy (in *Les Liposomes*, Puisieux and Delattre, Editors, Techniques et Documentation Lavoisier, Paris, pp.41-73 (1985)) summarize the methods which have been used to make MLV's.

The early lipid vesicle or liposome studies used phospholipids as the lipid source for the bilayers. The reason for this choice was that phospholipids are the principal structural components of natural membranes. However, there are many problems using phospholipids as artificial membranes or vesicles. First, isolated phospholipids are subject to degradation by a large variety of enzymes. Second, the most easily available phospholipids are those from natural sources, e.g., egg yolk lecithin, which contain polyunsaturated acyl chains that are subject to autocatalyzed peroxidation. When peroxidation occurs, the lipid structure breaks down, causing premature release of encapsulated materials and the formation of toxic peroxidation byproducts. This problem can be avoided by hydrogenation but hydrogenation is an expensive process, thereby raising the cost of the starting materials. Cost is a third problem associated with the use of phospholipids on a large scale. For example, a kg of egg yolk lecithin pure enough for pharmacological liposome production presently costs in excess of $1,000.

Recently, there has been some indication that commercially available surfactants might be used to form the lipid bilayer in liposome-like multilamellar lipid vesicles (see, e.g., L'Oreal patent no. 4,217,344, and copending U.S. Pat. application No. 457,571). Both surfactants and phospholipids are amphiphiles, having at least one lipophilic acyl or alkyl group attached to a hydrophilic head group. The head groups are attached to one or more lipophilic chains by ester or ether linkages.

However, even non-phospholipid vesicles may be fragile, resulting in the risk of releasing potentially harmful encapsulated materials to the immediate environment. Therefore, the development of a carrier with added mechanical strength would satisfy a long felt need in the field of material encapsulation and transport.

Accordingly, an object of the invention is to provide paucilamellar lipid vesicles from non-phospholipid materials having added mechanical strength.

Another object of the invention is to provide a method of producing reinforced Paucilamellar lipid vesicles which is rapid, and which involves the use of relatively inexpensive materials Yet another object of the invention is to provide a stronger vehicle for transport of oil soluble and aqueous materials.

A further object of the invention is to provide a method of encapsulating oily and aqueous materials in lipid vesicles useful for transport of such materials.

These and other objects and features of the invention will be apparent from the following detailed description.

SUMMARY OF THE INVENTION

The present invention features polyacrylamide-reinforced paucilamellar lipid vesicles for use as carriers of either hydrophobic or hydrophilic materials, and a method for their manufacture. The invention further features the use of reinforced paucilamellar lipid vesicles to encapsulate and transport a broad spectrum of materials.

Reinforced paucilamellar lipid vesicles of the present invention are composed of about 2-10 lipid bilayers in the form of substantially spherical shells separated by a plurality of aqueous layers. Each of the bilayers has a layer of polymerized acrylamide (polyacrylamide) lining its innermost side. The lipid bilayers and aqueous layers surround a large, substantially amorphous central cavity, which, in one embodiment contains a water-immiscible oily phase, and may include an oil-soluble or oil-dispersible material. In an alternative embodiment, the central cavity contains a polyacrylamide core. In addition, the aqueous layers may also include an aqueous-soluble material.

The bilayers contain a surfactant preferably selected from the group consisting of:

polyoxyethylene fatty acid esters having the formula $R_1\text{-COO}(C_2H_4O)_n H$ where $n = 2-10$, and $R_1$ is the residue derived from a carboxylic acid selected from the group consisting of lauric, myristic, cetyl, stearic, and oleic acids, and derivatives thereof;

polyoxyethylene fatty acid ethers having the formula $R_2\text{-CO}(C_2H_4O)_m H$ where $m = 2-4$, and $R_2$ is the residue derived from a carboxylic acid selected from the group consisting of lauric, myristic, and cetyl acids, single or double unsaturated octadecyl acids, double unsaturated eicodienoic acids, and derivatives thereof;

diethanolamides having the formula $(HOCH_2\text{-}CH_2)_2 NCO\text{-}R_3$ where $R_3$ is the residue derived from a carboxylic acid selected from the groups consisting of caprylic, lauric, myristic, and linoleic acids, and derivatives thereof;

long chain acyl hexosamides having the formula $R_4\text{-NOCO-}(CH_2)_b\text{-}CH_3$ where $b = 10-18$, and $R_4$ is the residue derived from a sugar molecule selected from the group consisting of glucosamine, galactosamine, and N-methylglucamine;

long chain acyl amino acid amides having the formula $R_5\text{-CHCOOH-NOC-}(CH_2)_c\text{-}CH_3$ where $c = 10-18$, and $R_5$ is an amino acid side chain;

long chain acyl amides having the formula $HOOC\text{-}(CH(CH_2)_d\text{-}NCH_3\text{-NCO-}R_6$ where $d = 1-3$, and $R_6$ is an acyl chain having 12-20 carbons and not more than two unsaturations;

polyoxyethylene glyceryl monostearate with 1-10 polyoxyethylene groups; and glycerol monostearate, glycerol monooleate, or glycerol monopalmitate.

In some embodiments, the lipid bilayers further contain a steroid preferably selected from the group consisting of cholesterol, hydrocortisone, and analogs and derivatives thereof. In addition, the bilayers may include a charge-producing agent such as a negative charge-producing agent selected from the group consisting of carboxylic acids, e.g., oleic or palmitic acids, dicetyl phosphate, cetyl sulphate, phosphatidic acid, phosphatidyl serine, and mixtures thereof, or a positive charge-producing agent selected from the group consisting of long chain amines such as stearyl amines and oleylamines, long chain pyridinium compounds such as cetylpyridinium chloride, quaternary ammonium compounds, and mixtures thereof.

The polyacrylamide lining the innermost side of each bilayer, and in some embodiments, substantially filling the central cavity, preferably includes about 1-30 per cent by weight acrylamide.

In some aspects of the invention, the water-immiscible oily phase in the central cavity contains an oily material preferably selected from the group consisting of oils, waxes, natural and synthetic triglycerides, acyl esters, petroleum derivatives, and analogs and derivatives thereof. Alternatively, the central cavity may contain a core of polyacrylamide.

The method for making the reinforced paucilamellar lipid vesicles of the present invention includes the following steps. A lipophilic phase containing a surfactant and a lipid-soluble material to be encapsulated or to be incorporated into the lipid structure of the vesicle is formed.

An aqueous phase containing acrylamide is also formed. This aqueous phase is mixed under shear mixing conditions with the lipophilic phase to form a plurality of paucilamellar lipid vesicles containing acrylamide in the aqueous regions. "Shear mixing" is defined as the mixing of the lipophilic phase with the aqueous phase under turbulent or shear conditions which provide adequate mixing to hydrate the lipid and form lipid vesicles. A separable hydrated lamellar phase is not formed by shear mixing but rather any planar lamellae which form are disrupted as they form.

The vesicles so formed are separated from any unincorporated vesicle constituents. The acrylamide in the aqueous regions of the vesicles is polymerized, thereby forming the reinforced lipid vesicles of the present invention.

In one embodiment of the invention, a water-immiscible oily phase is formed, which, in preferred aspects, contains an oil-soluble or oil-dispersible material. The lipophilic phase and the oily phase are blended to form a lipid dispersion. The term "dispersion" as used herein includes a suspension or colloid yielding a flowable phase. This dispersion is then shear-mixed with the aqueous phase. After separating the paucilamellar vesicles from the unincorporated vesicle constituents and allowing the acrylamide to polymerize, polyacrylamide-reinforced vesicles are formed having the oily phase in the central cavity.

The invention also includes a method of encapsulating a water-soluble material. In this method, the material to be encapsulated is dissolved in the aqueous phase.

BRIEF DESCRIPTION OF THE DRAWINGS

The foregoing and other objects of this invention, the various features thereof, as well as the invention itself, may be more fully understood from the following description when read together with the accompanying drawing in which.

DETAILED DESCRIPTION OF PREFERRED EMBODIMENTS

Figure 1:
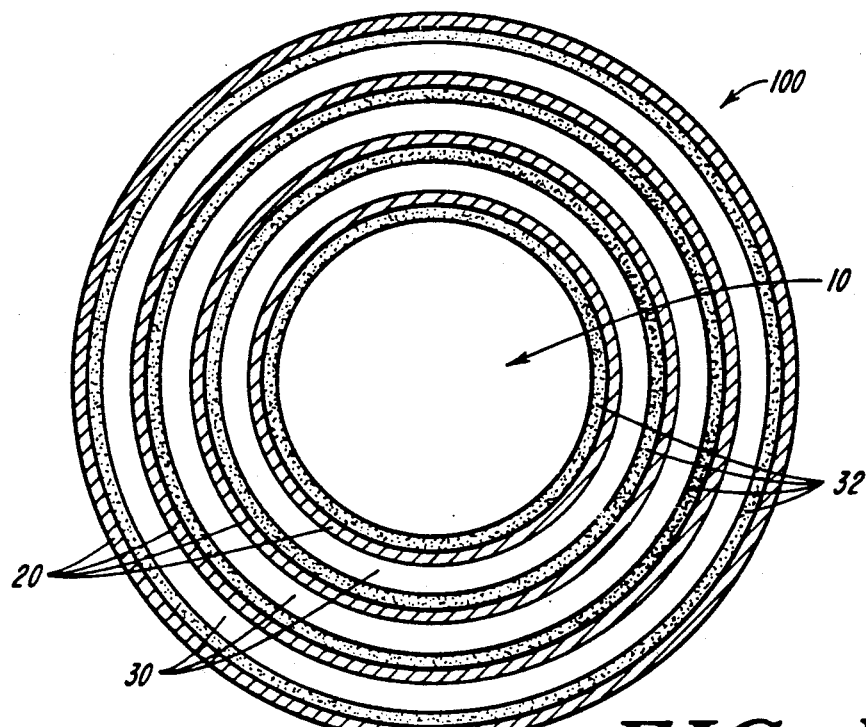
FIG. 1 is a schematic illustration of one embodiment of the invention, including an acrylamide-reinforced paucilamellar lipid vesicle with an oil filled central cavity.

The methods and materials disclosed herein for the production of the polyacrylamide-reinforced paucilamellar lipid vesicles yield reinforced vesicles with either a high oil or aqueous volume. FIG. 1 illustrates a reinforced vesicle 100 having an oil-filled central cavity or core. A large, substantially amorphous center cavity 10 is surrounded by a plurality of lipid bilayers 20 having aqueous layers 30 interspersed therebetween. About four lipid bilayers is standard with 2-10 possible. Each of bilayers 20 have a layer of polyacrylamide 32 lining their innermost side. The amorphous center region 10 may be partially or totally filled with an oily material, forming oil core, polyacrylamide-reinforced PLV's. If oil is not used, the polyacrylamide may fill the central cavity 10.

The oil core, polyacrylamide-reinforced vesicles of the invention have the advantage that a large central volume can permit the encapsulation of large particles which either are dissolved in the oil as well as particles in the form of suspensions or colloids (i.e., are oil-dispersible). Particles such as paint pigments can be encapsulated in this manner.

Figure 2:
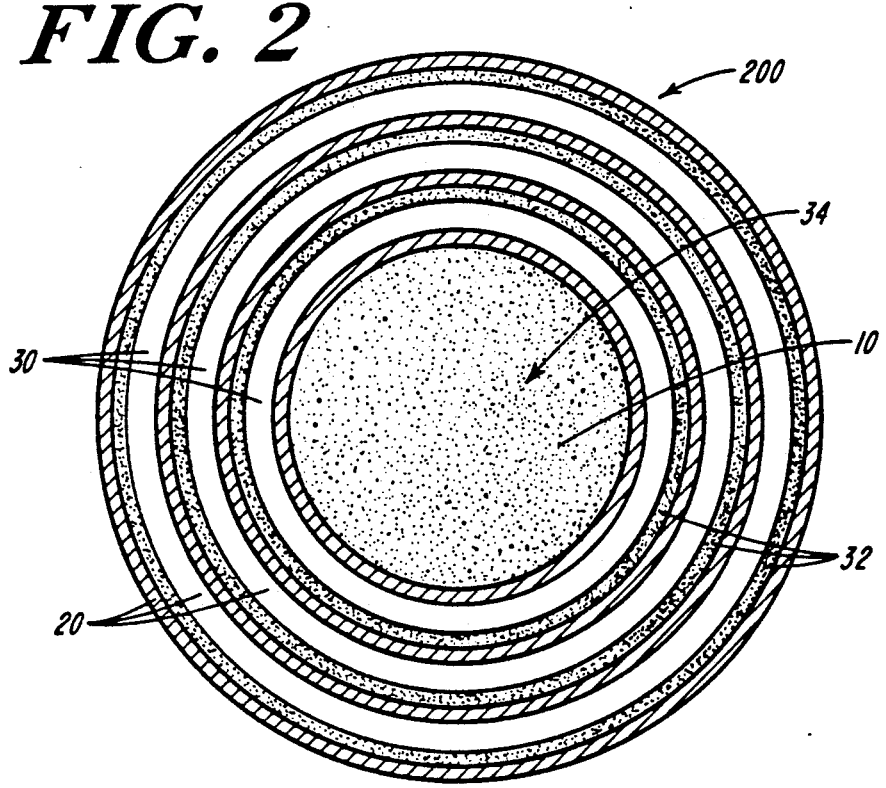
FIG. 2 is a schematic illustration of another embodiment of the invention, including an acrylamide-reinforced paucilamellar lipid vesicle having a polyacrylamide core.

FIG. 2 is a schematic illustration of a reinforced vesicle 200 having a polyacrylamide core 34 substantially filling central cavity 10. The lipid bilayers of the vesicles are formed from a surfactant such as polyoxyethylene fatty acid esters and ethers of various formulae, diethanolamines, long chain hexosamides, acyl amino acid amides, and acyl amides of various formulae, polyoxyethylene glyceryl monostearates, and glycerol monostearate, glycerol palmitate, or glycerol oleate. Commercially available surfactants include the BRIJ family of Polyoxyethylene acyl ethers, (available from ICI Americas, Inc. of Wilmington, DE).

A steroid may also be incorporated into the bilayers to improve the thermotropic phase transition properties of the vesicle, as well as to permit the manufacture of some vesicles which will not otherwise be possible. Useful steroids include cholesterol, hydrocortisone, and any derivatives and analogs thereof.

For certain uses, the incorporation of a charge-producing amphiphile, yielding, for example, a net negative charge to the lipid vesicles, is helpful. The preferred negative charge-producing materials are carboxylic acids, e.g., palmitic or oleic acid, dicetyl phosphate, cetyl sulphate, phosphatidic acid, phosphatidyl serine, and mixtures thereof. In order to provide a net positive charge to the vesicles, long chain amines, e.g., stearyl amines or oleyl amines, long chain pyridinium compounds, e.g., cetyl pyridinium chloride, quaternary ammonium compounds, or mixtures of these can be used.

Paucilamellar lipid vesicles reinforced with polyacrylamide have added mechanical strength due to the presence of the polyacrylamide. These vesicles may be used where microcapsules or other types of non-lipid carriers have previously been used, e.g., as paint or dye carriers, and may be employed as carriers of various types of organic and non-organic materials.

The reinforced paucilamellar lipid vesicles can be made by a variety of devices which provides sufficiently high shear for shear mixing. These include a syringe, a microfluidizer such as is made by Biotechnology Development Corporation, a French press, and other devices which provide a high enough shear force and the ability to handle heated, semiviscous lipids. If a very high shear device is used, it may be possible to microemulsify powdered lipids, under pressure, at a temperature below their normal melting points, and still form the lipid vesicles of the present invention.

A device which is particularly useful for making the lipid vesicles of the present invention has been developed (Micro Vesicular Systems, Inc., Vineland, NJ), and is further described in U. S. Patent application Ser. No. 163,806, now U.S. Pat. No. 7,895,452 herein incorporated by reference. Briefly, this device has a substantially cylindrical mixing chamber with at least one tangentially located inlet orifice. One or more orifices lead to a reservoir for the lipophilic phase, mixed with an oil phase if lipid-core PLV's are to be formed, and at least one of the other orifices is attached to a reservoir for the aqueous phase. The different phases are driven into the cylindrical chamber through pumps, e.g., positive displacement pumps, and intersect in such a manner as to form a turbulent flow within the chamber. The paucilamellar lipid vesicles containing acrylamide form rapidly, e.g., less than 1 second, and are removed from the chamber through an axially located discharge orifice. The acrylamide is easily polymerized, forming the final vesicles.

In order to achieve the proper blending necessary to form the reinforced paucilamellar lipid vesicles, all of the materials are normally in a flowable state. However, in the process of the present invention, use of a solvent for the surfactant (the classic method of producing multilamellar lipid vesicles) is not only unnecessary; it is counter-productive. Many of the surfactants useful in the invention are liquids at room temperature or at slightly elevated temperatures, requiring only gentle heating for flowability. Even the most difficult surfactants of the group to use, e.g., glycerol monostearate, can be easily handled at approximately 70° C. Therefore, one standard procedure is to elevate the temperature of the lipophilic phase in order to make it flowable followed by carrying out the shear mixing between the lipophilic phase and the aqueous phase at a temperature whereat such that both phases are liquids. While it is often desirable to use the same temperature for both phases, this is not always necessary.

The aqueous phase, when shear mixed with the lipophilic phase, contains acrylamide in unpolymerized form dissolved therein. After formation of the paucilamellar vesicles, the acrylamide within the vesicle's aqueous regions (i.e., between the lipid bilayers and, in the absence of an oily material, in the central cavity) is then allowed to polymerize. Polymerization may occur, for example, at room temperature with time upon the addition of a polymerization initiator or catalyst such as N,N,N',N'-tetraethylmethylethylene diamine ("TEMED"). Alternatively, polymerization may be initiated by light or heat. When polymerized, the polyacrylamide becomes a gel whose firmness is dependent on the percentage of acrylamide in the aqueous solution, e.g., vesicles containing 18%–30% polyacrylamide are more firm than those containing lower percentages such as 1.5%, 3%, or 12%. In addition, the greater the concentration of acrylamide, the thicker the layer of polyacrylamide formed in the central region lining the inner most bilayer. Polyacrylamide concentrations are therefore chosen according to the proposed use, and hence required additional strength, of the vesicle. If paucilamellar vesicles encapsulating an aqueous material are desired, a lower percentage of acrylamide is desirable, making extraction of the material from the central cavity more easy to carry out.

Vesicle constituents which have not been incorporated are then removed, for example, by known washing techniques including dialysis or vesicle resuspension, followed by centrifugation or sedimentation.

The invention, and its many uses, will be more apparent from the following, non-limiting Examples.

EXAMPLE 1

Reinforced paucilamellar lipid vesicles with oily cores were prepared from a lipid mixture of polyoxyethylene 2 cetyl ether (BRIJ 52, ICI Americas, Inc., Wilmington, DE) (74.2 g), cholesterol (23.16 g), and oleic acid (3.2 g) as the lipophilic phase, mineral oil as the oily phase, and 12% polyacrylamide as the aqueous phase.

A 12% acrylamide solution made from 10mM Tris-HCl, pH 7.0, and 30%/0.8% acrylamide/bis-acrylamide (Sigma Chemical Co., St. Louis, MO), and 10 $\mu$l TEMED (Sigma Chemical Co., St. Louis, MO) was prepared.

The lipophilic phase was blended with the oily phase to form a lipid dispersion as follows: 0.3 ml of the lipid mixture was blended with 2.0 ml mineral oil (Heavy Duty, CVS Pharmacy) by placing them in a 5 ml syringe and heating to 40° C., a temperature above the melting point of the lipid. This lipid dispersion was forcibly injected, via a three-way stopcock, into 1.5 ml of an aqueous phase containing 12% acrylamide solution. The aqueous solution, which was contained in a 25 ml syringe, was also at 40°. The process of injection of the lipophilic phase into the aqueous phase took less than five seconds. The resulting mixture was then forced into a second 25 ml syringe at a linear flow rate of 8–12 m/s through an orifice about 1 mm in diameter. The mixture was driven continuously back and forth between the two syringes for approximately 2 minutes, thereby providing the shear mixing necessary to make the high volume reinforced paucilamellar lipid vesicles. A milky suspension containing the reinforced paucilamellar lipid vesicles resulted. This was mixed with 5 ml 20% dextran in 10 mm Tris-HCl, pH 7.4, and the vesicles freed of excess acrylamide by centrifugation (10,000 rpm, 15 min.; Beckman J2 centrifuge, Palo Alto, CA, causing the paucilamellar vesicles to collect in a low-density layer atop the aqueous solution. The vesicles were placed at room temperature for two hours to allow the acrylamide to polymerize.

After the polymerization step and another washing using 20% dextran, the vesicles redispersed easily as individual (unaggregated) particles of about 1 micron in diameter by optical microscopy An aliquot of vesicles was dissolved with 3:1 chloroform/methanol (vol/vol) which dissolves the vesicle wall components. An oil layer was formed above a chloroform/methanol layer which was found above a pellet consisting of unaggregated acrylamide beads. These results indicate that the acrylamide and the oil had been incorporated into the vesicles, and that the acrylamide had polymerized within the vesicles.

EXAMPLE 2

Reinforced lipid vesicles containing the same surfactant as the lipophilic phase, but having a core of peanut oil in place of mineral oil, and including 18% acrylamide containing crystal violet as a tracer, were prepared essentially as described in Example 1.

After washing, the vesicles were extracted with 99% ethanol which dissolves the vesicle wall components. A layer of oil was found atop the dye-containing ethanol solution, and tiny polyacrylamide beads were found in the pellet, indicating that the dye and oil had been incorporated into the vesicles, and that the acrylamide had polymerized in the vesicles.

EXAMPLE 3

Reinforced paucilamellar lipid vesicles containing encapsulated protein, a water-soluble material, were formed essentially as described in Example 1, but excluding mineral oil and using 5% acrylamide and 1% bovine serum albumin (BSA) in the aqueous phase. After polymerization, washing, and solvent extraction, the polyacrylamide bead pellet was stained with Coomassie Brilliant Blue essentially as described by Fairbanks, Steck, and Wallach (Biochem. (1971) 10 2606-2617). After removing excess stain, the beads retained a blue color, indicating the presence of polyacrylamide-entrapped BSA. The BSA can be eluted by prolonged extraction with 10% sodium dodecyl sulfate (SDS). Chemical analysis showed that more than 80% of the encapsulated protein (BSA) was polyacrylamide-associated.

As can be seen from the results of these examples, polyacrylamide reinforced paucilamellar lipid vesicles having high oil or aqueous uptake volume can be formed with the materials and methods of the present invention.

The foregoing description is illustrative only and those skilled in the art may find other materials and methods which accomplish the same results. Such other materials and methods are included within the following claims.

What is claimed is:

1. A reinforced paucilamellar lipid vesicle comprising 2-10 lipid bilayers in the form of substantially spherical shells separated by aqueous layers, each of said bilayers having a layer of polyacrylamide lining the innermost side of each of said bilayers, and said lipid bilayers and aqueous layers surrounding a large, substantially amorphous central cavity containing a water-immiscible oily phase.

2. The vesicle of claim 1 wherein said central cavity further comprises polyacrylamide.

3. The reinforced vesicle of claim 1 wherein said lipid bilayers comprise a surfactant.

4. The reinforced vesicle of claim 3 wherein said surfactant is selected from the group consisting of (a) polyoxyethylene fatty acid esters having the formula $$R_1\text{-COO}(C_2H_4O)_n H$$

where $n = 2-10$, and $R_1$ is the residue derived from a carboxylic acid selected from the group consisting of lauric, myristic, cetyl and stearic, acids, (b) polyoxyethylene fatty acid ethers having the formula $$R_2\text{-CO}(C_2H_4O)_m H$$

where $m = 2-4$, and $R_2$ is the residue derived from a carboxylic acid selected from the group consisting of lauric, myristic, and cetyl acids, single or double unsaturated octadecyl acids, and double unsaturated eicodienoic acids, (c) diethanolamides having the formula $$(HOCH_2\text{-}CH_2)_2 NCO\text{-}R_3$$

where $R_3$ is the residue derived from a carboxylic acid selected from the group consisting of caprylic, lauric, myristic, and linoleic acids, (d) long chain acyl hexosamides having the formula $$R_4\text{-NOCO-}(CH_2)_b\text{-}CH_3$$

where $b = 10-18$, and $R_4$ is the residue derived from a sugar molecule selected from the group consisting of glucosamine, galactosamine, and N-methylglucamine, (e) long chain acyl amino acid amides having the formula $$R_5\text{-CHCOOH-NOC-}(CH_2)_c\text{-}CH_3$$

where $c = 10-18$, and $R_5$ is an amino acid side chain, (f) long chain acyl amides having the formula $$HOOC\text{-}(CH_2)_d\text{-NCH}_3\text{-}(CH_2)_3\text{-NCO-}R_6$$

where $R_6$ is an acyl chain having 12-20 carbons and not more than two unsaturations, and $d = 1-3$, (g) polyoxyethylene glyceryl monostearate with 1-10 polyoxyethylene groups, and (h) glycerol monostearate, monooleate or monopalmitate.

5. The reinforced vesicle of claim 1 wherein said lipid bilayers further comprise a steroid.

6. The reinforced vesicle of claim 5 wherein said steroid is selected from the group consisting of cholesterol, hydrocortisone, and mixtures thereof.

7. The reinforced vesicle of claim 1 wherein said lipid bilayers further comprise a charge-producing agent.

8. The reinforced vesicle of claim 7 wherein said charge-producing agent is a negative charge-producing agent selected from the group consisting of carboxylic acids, dicetyl phosphate, cetyl sulphate, phosphatidic acids, phosphatidyl serine, and mixtures thereof.

9. The reinforced vesicle of claim 7 wherein said charge-producing agent is a positive charge-producing agent selected from the group consisting of long chain amines, long chain pyridinium compounds, quaternary ammonium compounds, and mixtures thereof.

10. The reinforced vesicle of claim 1 wherein said aqueous layers comprise about 1-30 percent by weight acrylamide.

11. The reinforced vesicle of claim 1 wherein said water-immiscible oily phase is selected from the group consisting of oils, waxes, natural and synthetic triglycerides, acyl esters, petroleum derivatives, and mixtures thereof.

12. A method of making reinforced paucilamellar lipid vesicles comprising the steps of:

forming a lipophilic phase containing a surfactant and any lipid-soluble material to be incorporated into the lipid structure of the bilayers;

forming a water-immiscible oily phase;

blending said lipophilic phase and said oily phase to form a lipid dispersion;

forming an aqueous phase containing shear mixing said lipid dispersion and said aqueous phase, thereby forming a plurality of paucilamellar vesicles, each of said vesicles having a water-immiscible oily phase encapsulated in said central cavity, whereby each of said vesicles have about 2-10 lipid bilayers in the form of substantially spherical shells separated by a plurality of aqueous layers containing acrylamide, said lipid bilayers and aqueous layers surrounding a large, substantially amorphous cavity region;

separating said vesicles from any unincorporated vesicle constituents; and polymerizing said acrylamide in said aqueous layers, thereby forming said reinforced paucilamellar lipid vesicles.

13. The method of claim 12 wherein said lipophilic phase-forming step further comprises forming a lipophilic phase containing a surfactant selected from the group consisting of (a) polyoxyethylene fatty esters having the formula $$R_1\text{-}COO(C_2H_4O)_nH$$

where $n = 2\text{-}10$, and $Rh_1$ is the residue derived from a carboxylic acid selected from the group consisting of lauric, myristic, cetyl and stearic, acids, (b) polyoxyethylene fatty acid ethers, having the formula $$R_2\text{-}CO(C_2H_4O)_mH$$

where $m = 2\text{-}4$, and $R_2$ is the residue derived from a carboxylic acid selected from the group consisting of lauric, myristic, and cetyl acids, single and double unsaturated octadecyl acids, and double unsaturated eicodienoic acids, (c) diethanolamides, having the formula $$(HOCH_2\text{-}CH_2)_2NCO\text{-}R_3$$

where $R_3$ is the residue derived from a carboxylic acid selected from the group consisting of caprylic, lauric, myristic and linoleic acids, (d) long chain acyl hexosamides having the formula $$R_4\text{-}NOCO\text{-}(CH_2)_b\text{-}CH_3$$

where $b = 10\text{-}18$, and $R_4$ is the residue derived from a sugar molecule selected from the group consisting of glucosamine, galactosamine, and N-methylglucamine, (e) long chain acyl amino acid amides having the formula $$R_5\text{-}CHCOOH\text{-}NOC\text{-}(CH_2)_c\text{-}CH_3$$

where $c = 10\text{-}18$, and $R_5$ is an amino acid side chain, (f) long chain acyl amides having the formula $$HOOC\text{-}(CH_2)_d\text{-}NCH_3\text{-}(CH_2)_3\text{-}NCO\text{-}R_6$$

where $d = 1\text{-}3$, and $R_6$ is an acyl chain having 12-20 carbons and not more than two unsaturations, (g) polyoxyethylene glyceryl monostearate with 1-10 polyoxyethylene groups, and (h) glycerol monostearate, glycerol monooleate, or glycerol monopalmitate.

14. The method of claim 12 wherein said lipophilic phase-forming step includes forming a lipophilic phase comprising a steroid as said lipid-soluble material.

15. The method of claim 14 wherein said lipophilic phase-forming step further comprises forming a lipophilic phase containing a steroid selected from the group consisting of cholesterol, hydrocortisone, and mixtures thereof.

16. The method of claim 12 wherein said lipophilic phase-forming step comprises forming a lipophilic phase comprising a charge-producing agent as said lipid-soluble material.

17. The method of claim 16 wherein said lipophilic phase-forming step further comprises forming a lipophilic phase containing a negative charge-producing agent selected from the group consisting of carboxylic acid, dicetyl phosphate, cetyl sulphate, phosphatidic acid, phosphatidyl serine, and mixtures thereof.

18. The method of claim 16 wherein said lipophilic phase-forming step further comprises forming a lipophilic phase containing a positive charge-producing agent selected from the group consisting of long chain amines, long chain pyridinium compounds, quaternary ammonium compounds, and mixtures thereof.

19. The method of claim 12 wherein said oily phase-forming step further comprises forming an oily phase containing an oil-dispersible or oil-soluble material to be encapsulated in said central cavity.

20. The method of claim 12 wherein said oily phase-forming step comprises forming an oily phase which includes an oily material selected from the group consisting of oils, waxes, natural and synthetic triglycerides, acyl esters, petroleum derivatives, and mixtures thereof.

21. The method of claim 12, wherein said aqueous phase-forming step comprises forming an aqueous phase containing about 1-30 percent by weight acrylamide.

* * * * *